United States Patent [19]

Tutt

[11] Patent Number: 5,172,278

[45] Date of Patent: Dec. 15, 1992

[54] BUCKMINSTERFULLERENES FOR OPTICAL LIMITERS

[75] Inventor: Lee W. Tutt, Thousand Oaks, Calif.

[73] Assignee: Hughes Aircraft Company, Los Angeles, Calif.

[21] Appl. No.: 782,184

[22] Filed: Oct. 24, 1991

[51] Int. Cl.$^5$ .................. G02B 5/24; G02F 1/36; H01S 3/113

[52] U.S. Cl. .................. 359/885; 359/241; 359/361

[58] Field of Search .............. 359/241, 321, 361, 614, 359/885; 385/5, 143, 145; 372/11, 21

[56] References Cited

U.S. PATENT DOCUMENTS

| | | | |
|---|---|---|---|
| 3,509,063 | 4/1970 | Teague | 359/241 |
| 3,620,597 | 11/1971 | Schwartz et al. | 359/885 |
| 3,721,172 | 3/1973 | Frungel et al. | 359/321 |
| 4,657,345 | 4/1987 | Gordon | 359/321 |
| 5,080,469 | 1/1992 | McCahon et al. | 359/241 |

OTHER PUBLICATIONS

Tutt et al; Proc. SPIE, vol. 1307, pp. 315-326, Apr. 1990.
McCahon et al; Proc. SPIE, vol. 1307, pp. 304-314, Apr. 20, 1990.
Tutt et al; Opt. Lett., vol. 15, #12, pp. 700-702, Jun. 15, 1990.
Skumanich, A.; Chem. Phys. Lett., vol. 182, #5, pp. 86-90, Aug. 9, 1991.
W. Kratschmer et al, Nature, vol. 347, pp. 354-357 (1990).
H. Ajie et al, Journal of Physical Chemistry, vol. 94, pp. 8630-8633 (1990).
J. P. Hare et al, Chemical Physics Letters, vol. 177 (4,5), pp. 394-397 (1991).
F. Diederich et al, Science, vol. 252, pp. 548-551 (Apr. 26, 1991).
I. Amato, Science, vol. 252, p. 646 (May 3, 1991).
J. M. Hawkins et al, Science, vol. 252, pp. 312-313 (Apr. 12, 1991).
J. M. Hawkins et al, Journal of Organic Chemistry, vol. 55 pp. 6250-6252 (1990).
P. J. Fagan, Science, vol. 252, pp. 1160-1161 (May 24, 1991).
Arbogast et al Journal of Physical Chemistry, vol. 95, pp. 11-12 (1991).

Primary Examiner—Nelson Moskowitz
Attorney, Agent, or Firm—E. E. Leitereg; W. K. Denson-Low

[57] ABSTRACT

Optically sensitive materials (18) such as sensors or the human eye are passively protected against overexposure to high intensity light (20) in the visible region using a reverse saturable absorber (14) comprising one of a class of organic compounds known as buckminsterfullerene, such as $C_{60}$. As the intensity of incident light increases, the intensity of transmitted light also increases up to a saturation level, but above the saturation level, the transmitted light intensity remains substantially constant even with increasing intensity of incident light. $C_{60}$ has an unexpectedly low threshold for optical limiting action, is thermally stable, and is easily manufacturable into devices.

26 Claims, 6 Drawing Sheets

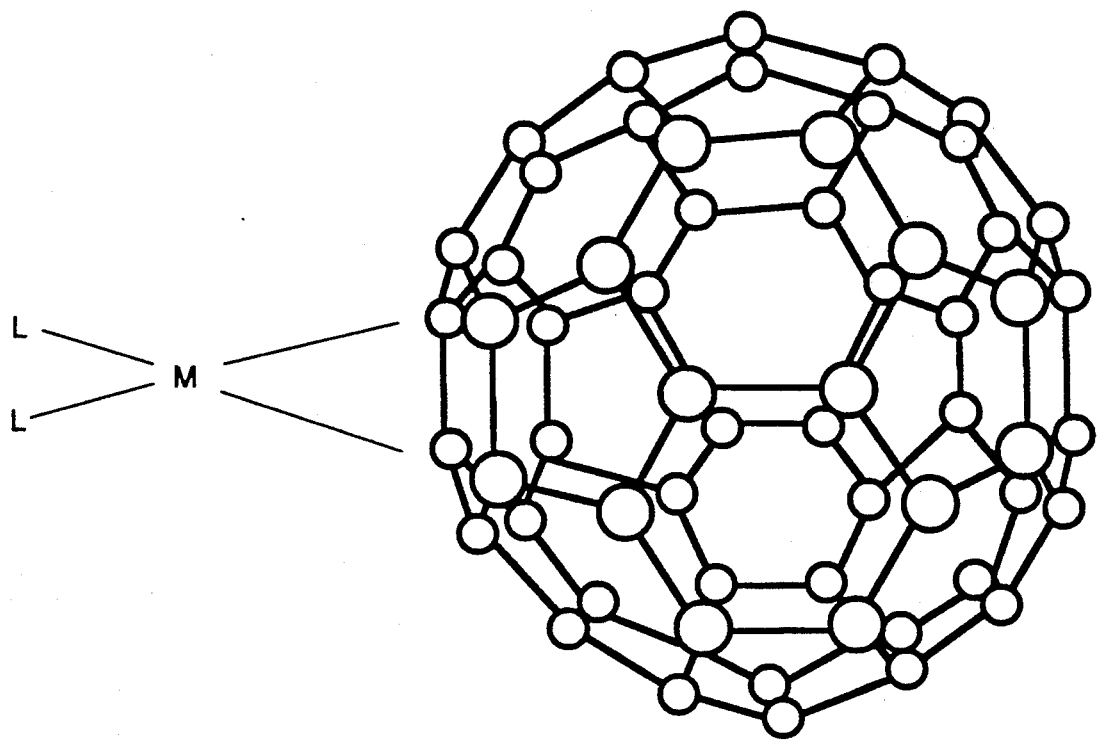
FIG. 6.
FIG. 7.
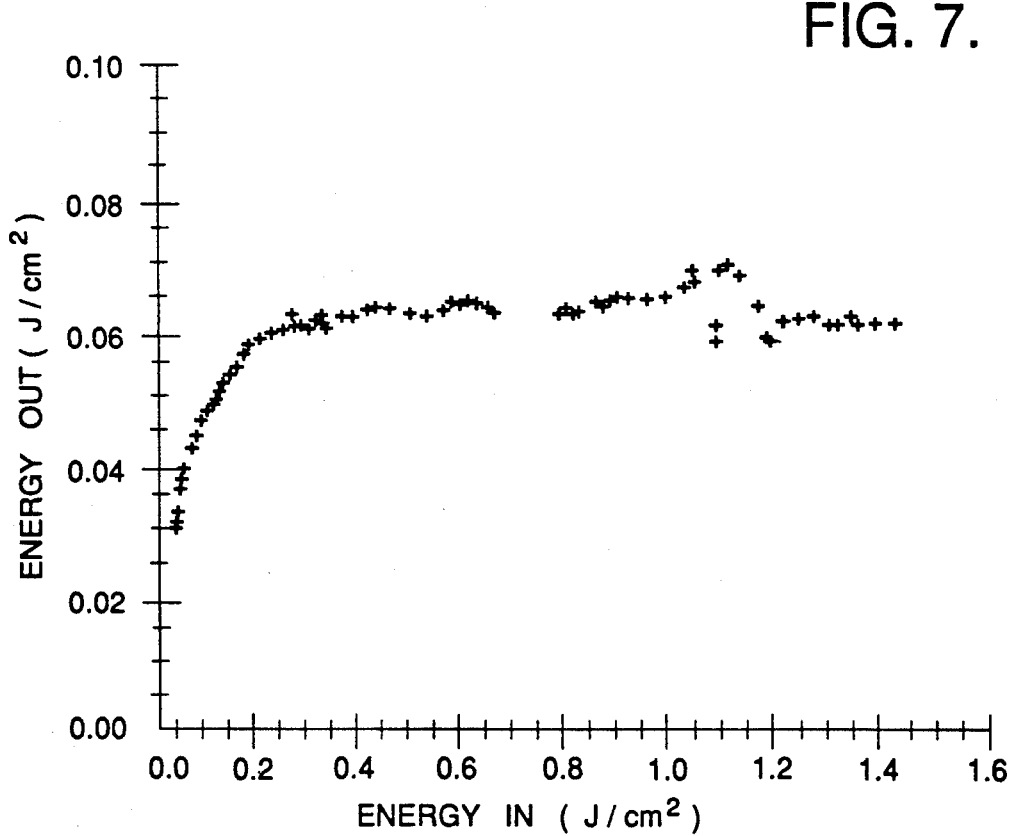

BUCKMINSTERFULLERENES FOR OPTICAL LIMITERS

BACKGROUND OF THE INVENTION

1. Field of the Invention

The present invention relates to light-absorbing materials, and, more particularly, to materials, called optical limiters, that passively protect optically sensitive materials from overexposure to high intensity light.

2. Description of Related Art

Optically sensitive materials such as optical sensors and the human eye are used to detect light because they contain components which are sensitive to light energy. In one common example, an optoelectronic sensor, such as an "electric eye", produces a voltage when light falls upon a sensing material within the sensor. However, such sensors can be "blinded" by overexposure to high intensity light, just as the human eye becomes blinded if it is exposed to overly intense light. In each case, exposure to high intensity light can temporarily or even permanently destroy the ability of the optically sensitive material to react to light.

There are two approaches to protecting such optically sensitive materials against blinding by overexposure to high intensity light. In the first, or "active" approach, when the electronic circuitry of the optically sensitive device detects a harmfully high intensity of light, it operates a mechanism to interpose a physical barrier between the light source and the optically sensitive material. The second, or "passive" approach, is employed when the onset of the harmful high-intensity light is so fast that no active system has the time to respond. In a passive protection system, a barrier is formed directly in response to the incident light. Such systems are called "optical limiters" and are characterized by the behavior that as the intensity of incident light increases, the intensity of light transmitted through the system also increases up to a saturation level. Above the saturation level, the transmitted light intensity remains substantially constant even with increasing intensity of incident light.

Organometallic compounds and some organics have been observed to show optical limiting characteristics, but all of the compounds suffer from at least one of the following: high optical intensity thresholds for optical limiting, undesirable manufacturing properties, or not effective over a broad band of optical radiation.

A desirable optical limiter would have a low optical intensity threshold for optical limiting, would be easy to manufacture, could be utilized in device manufacture, and would be effective over a reasonably broad bandwidth.

SUMMARY OF THE INVENTION

In accordance with the invention, a class of organic compounds, known as buckminsterfullerenes and their derivatives, are used to provide optical limiting for sensor protection applications. These compounds have an unexpectedly low threshold for optical limiting action, possess thermal stability, and sublime, which renders manufacturing in an optical limiting system very easy. Further, they are operable over a fairly broad band of optical radiation and are soluble in common organic solvents.

BRIEF DESCRIPTION OF THE DRAWINGS

FIGS. 1-6 represent various structures of buckminsterfullerenes and their derivatives;

FIG. 7, on coordinates of energy out (in $J/cm^2$) and energy in (in $J/cm^2$), is a plot of the light intensity transmitted by $C_{60}$ in toluene at 532 nm with 8 ns pulses;

DESCRIPTION OF THE PREFERRED EMBODIMENTS

Figure 1:
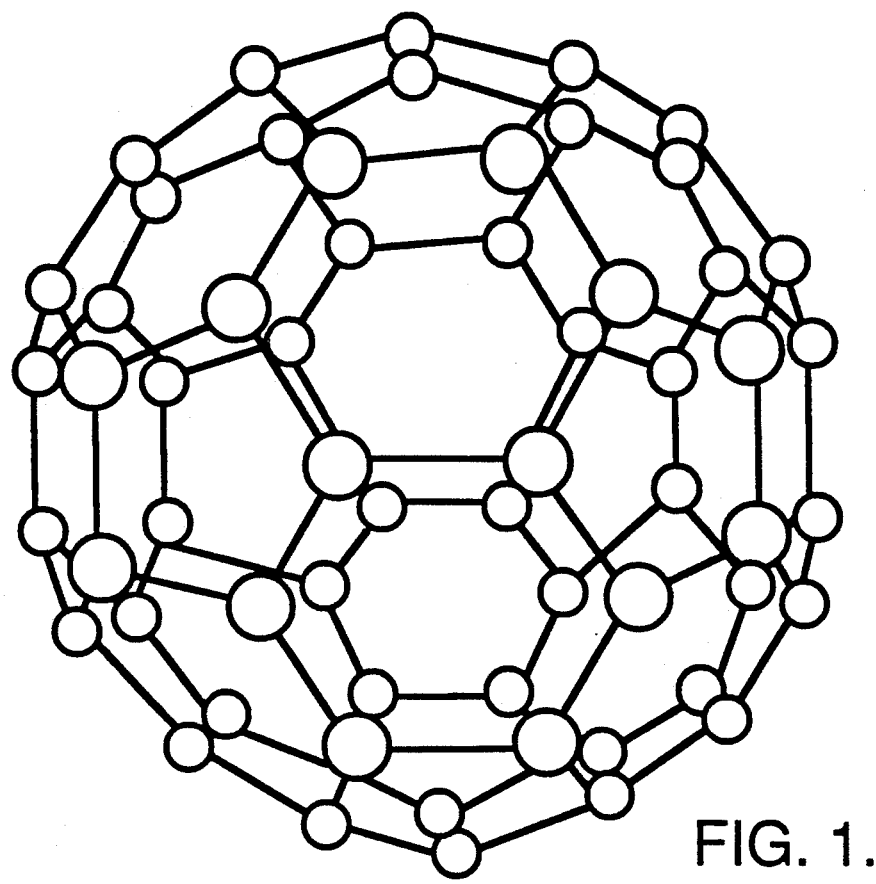
Figure 2:
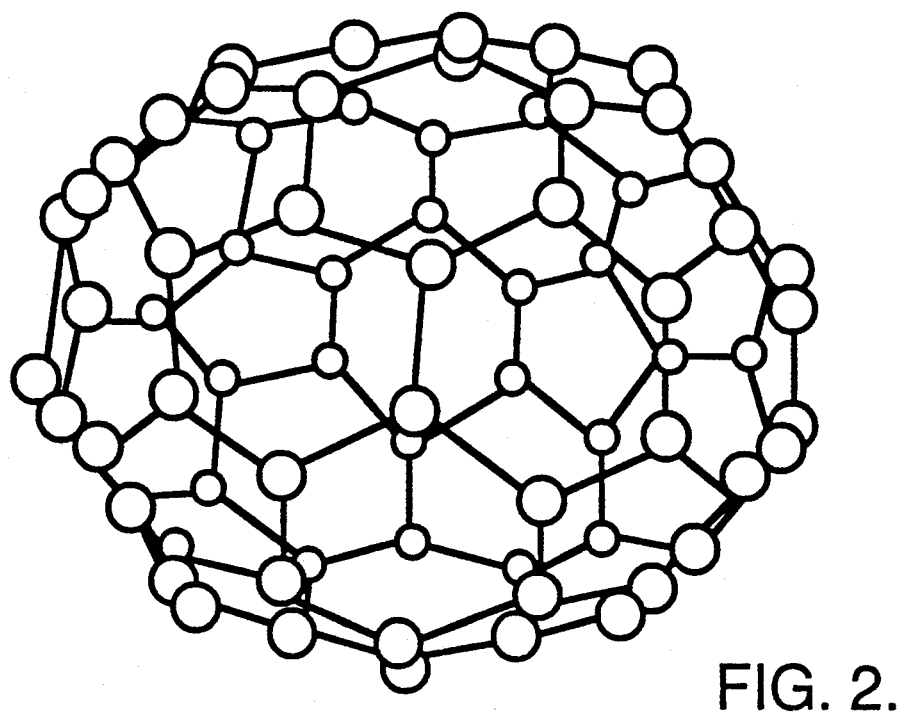

A variety of buckminsterfullerenes and their derivatives are depicted in FIGS. 1-6. FIG. 1 is a structural representation of $C_{60}$, while FIG. 2 is a structural representation of $C_{70}$. These compounds are carbon-only cages (or carbonaceous hollow cage molecules) and techniques for their formation are well-known; see, e.g., W. Krätschmer et al, *Nature*, Vol. 347, pp. 354-357 (1990), H. Ajie et al, *Journal of Physical Chemistry*, Vol. 94, pp. 8630-8633 (1990), and J. P. Hare et al, *Chemical Physics Letters*, Vol. 177 (4,5), pp. 394-397 (1991). Additional buckminsterfullerenes are also known; examples include $C_{76}$, $C_{84}$, $C_{90}$, and $C_{94}$, as described by F. Diederich et al, *Science*, Vol. 252, pp. 548-551 (Apr. 26, 1991).

Figure 3:
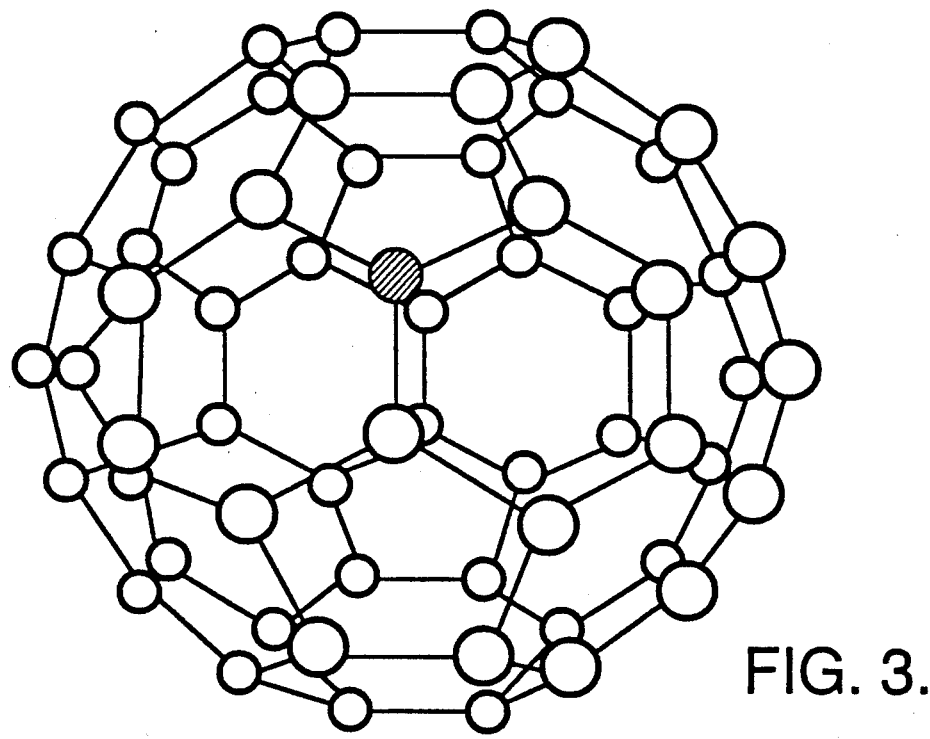
Figure 4:
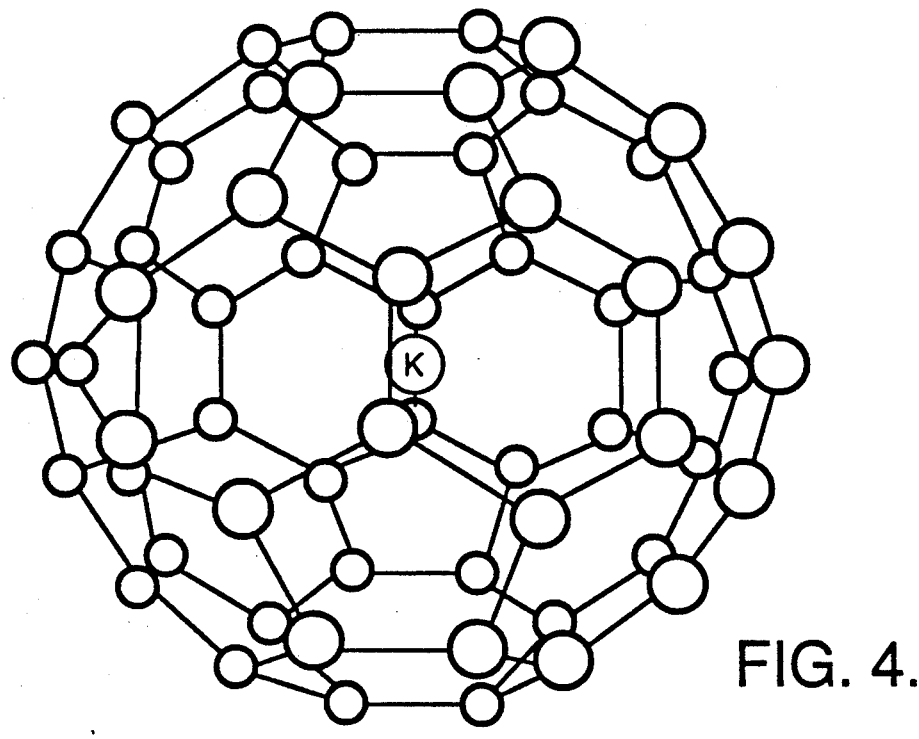
Figure 5:
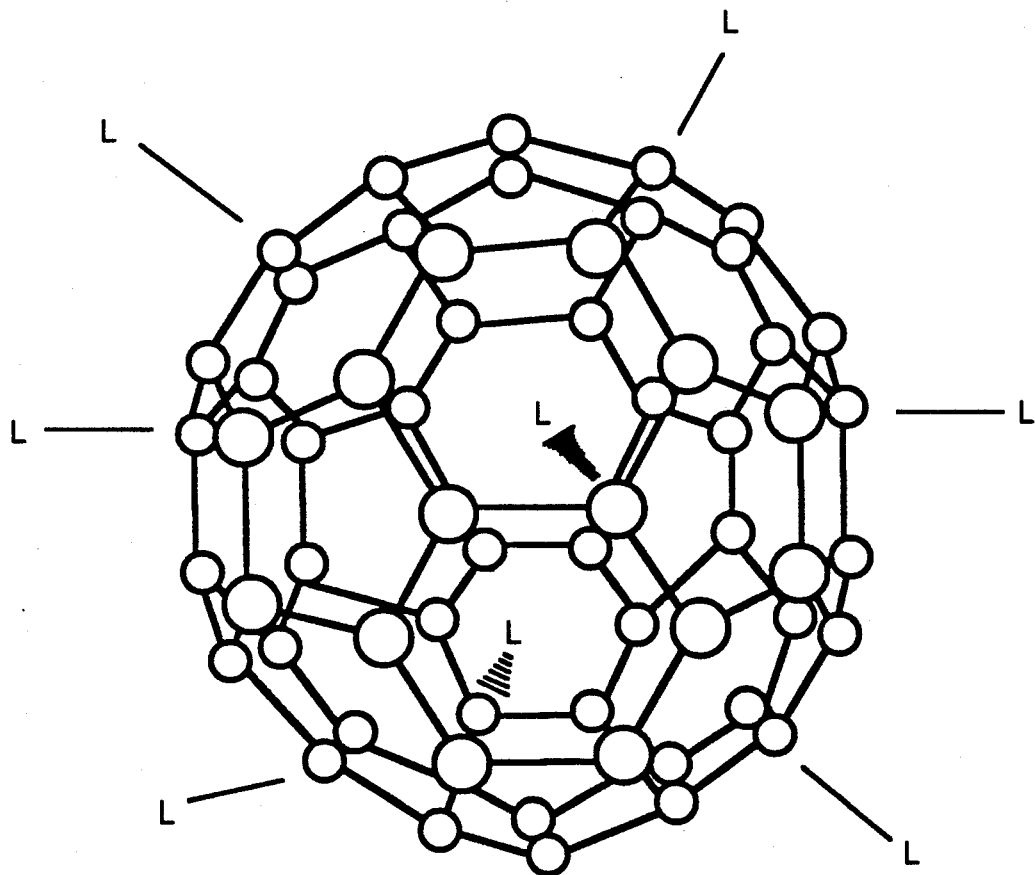

Modified buckminsterfullerenes (also known as "bucky-balls") are shown in FIGS. 3-6. FIG. 3 depicts $C_{59}B$, where a boron atom replaces one of the carbon atoms. FIG. 4 depicts $C_{60}K$, with the potassium atom (or other atom) caged inside the structure. FIG. 5 depicts "hairyballs", in which several ligands L are attached to various carbon atoms on the structure. FIG. 6 depicts an organometallic derivative, in which a metal atom M is bound to carbon atoms of the cage (here, two such carbon atoms) and has two ligands L associated therewith.

Boron replacement of carbon atoms and "hairyballs" are described, for example, by I. Amato, *Science*, Vol. 252, p. 646 (May 3, 1991). Organometallic derivatives are described, for example, by J. M. Hawkins et al, *Science*, Vol. 252, pp. 312-313 (Apr. 12, 1991), J. M. Hawkins et al, *Journal of Organic Chemistry*, Vol. 55, pp. 6250-6252 (1990), and P. J. Fagan, *Science*, Vol. 252, pp. 1160-1161 (May 24, 1991). $C_{70}O$ is another example of a fullerene derivative; see, Diederich, supra.

Examples of ligands include methyl, ethylenediamine, pyridine and tert-butyl pyridine (such as associated with osmium tetroxide adduct), triphenylphosphine (such as associated with platinum), and acetonitrile (such as associated with ruthenium).

The description which follows below is specifically directed to one buckyball, $C_{60}$. However, the same considerations apply to other buckyballs.

The compound $C_{60}$ acts as a good optical limiter (reverse saturable absorber). The compound absorbs more light as the incident intensity is increased, as shown in FIG. 7. This Figure shows the response of a toluene solution that is 63% transmitting (low intensity) at 532 nm to 8 ns 532 nm pulses of different intensities.

Figure 8:
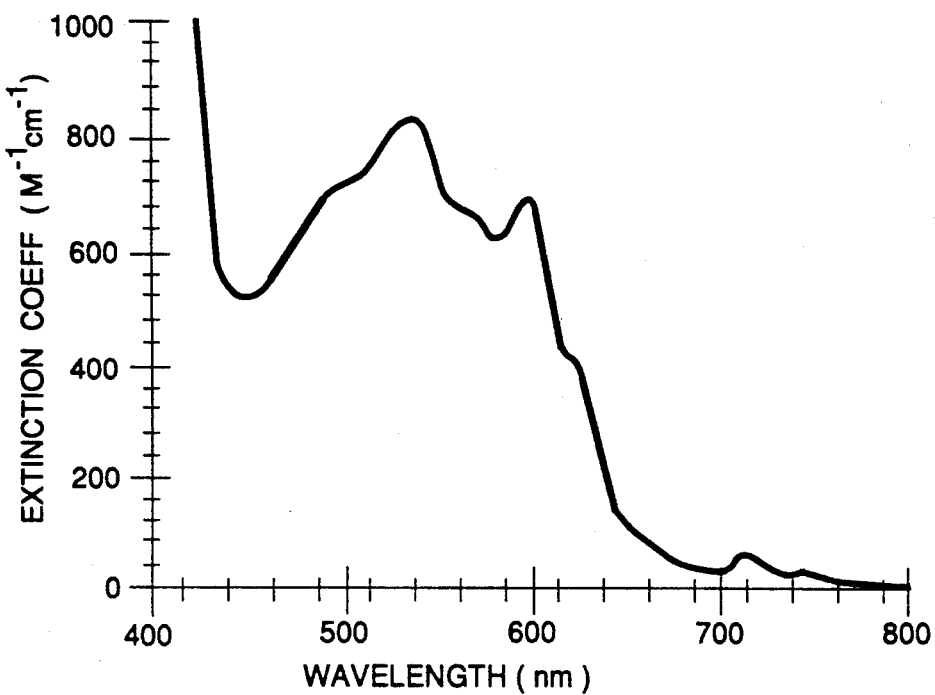
FIG. 8, on coordinates of extinction coefficient (in $M^{-1}cm^{-1}$) and wavelength (in nm), is a plot of the ground state absorption of $C_{60}$.

The low intensity absorption spectrum is shown in FIG. 8. This Figure, together with the triplet-triplet absorption spectrum of $C_{60}$ in benzene [reported by Arbogast et al in *Journal of Physical Chemistry*, Vol. 95, pp. 11–12 (1991)], indicates the optical limiting action should occur from at least about 420 to 550 nm, and perhaps even further. Such a bandwidth of at least about 130 nm, which is nearly one-half of the visible spectrum, is considered to be fairly broad for optical limiter applications.

The triplet state is very efficiently populated (>95% yield) and the lifetime in solution is known to be 40 microseconds in the absence of oxygen. This indicates the limiting action should be efficient for longer temporal optical pulses than previously possible. The triplet state acts as an accumulation site for electrons excited by pulses shorter than the lifetime. Longer temporal pulses cycle electrons back to the ground state, decreasing the absorption efficiency.

Figure 9:
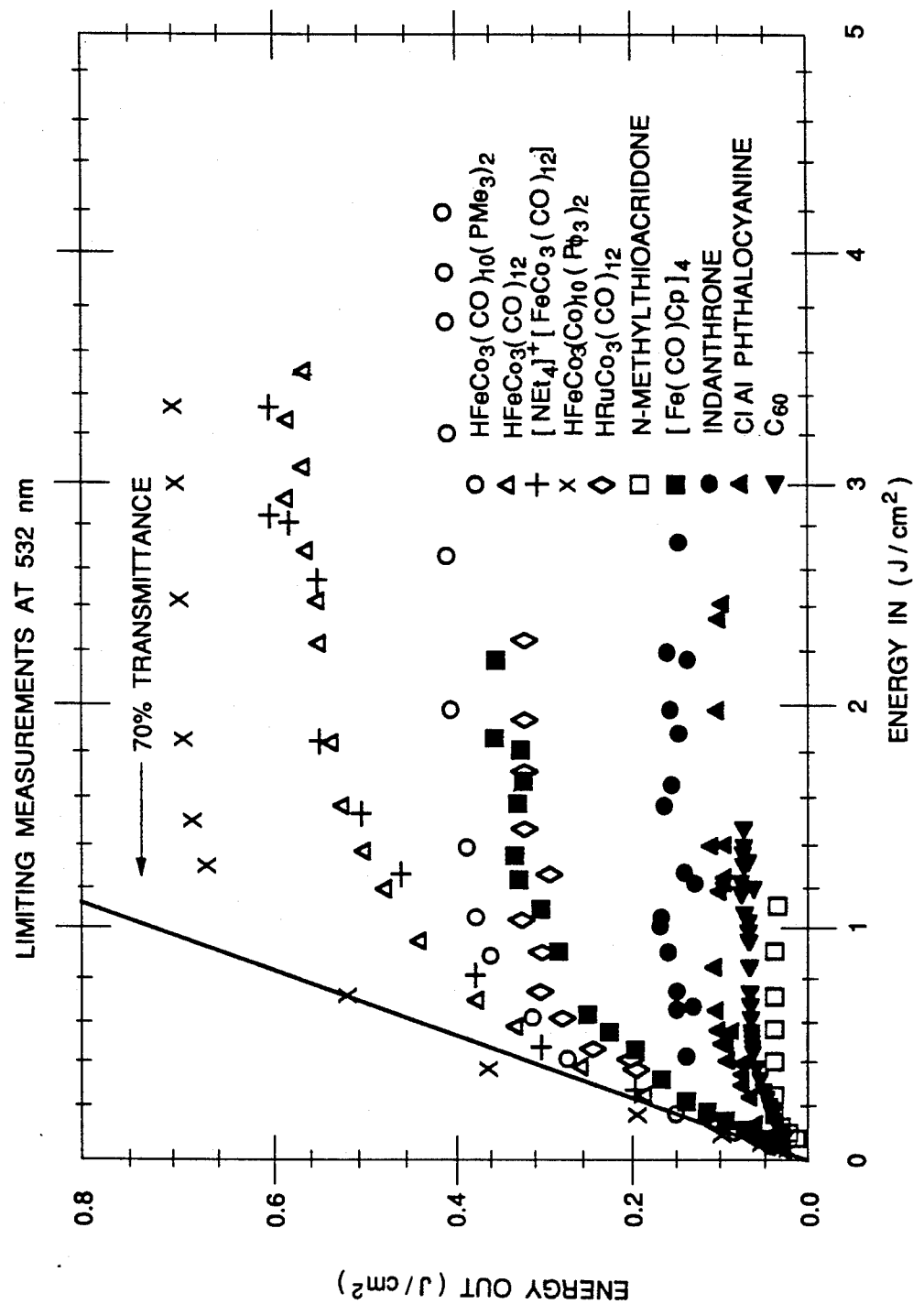
FIG. 9, on coordinates of energy out (in $J/cm^2$) and energy in (in $J/cm^2$), is a plot of optical limiting measurements at 532 nm with 8 ns pulses for a variety of prior art materials, compared to $C_{60}$.

In FIG. 9, the limiting action of $C_{60}$ is compared to other optical limiters. The only compound that closely compares is N-methylthioacridone, which is a narrow band optical limiter, having a bandwidth apparently less than about 50 nm.

Figure 10A:
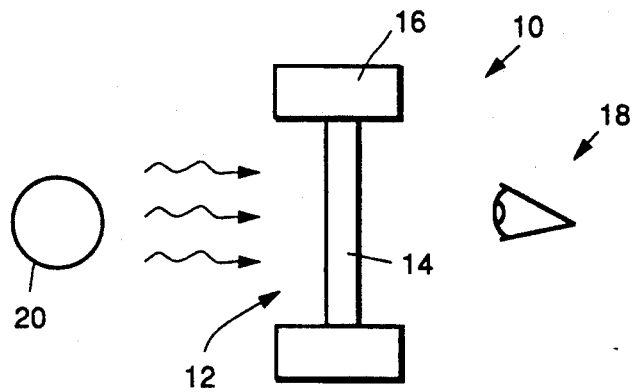
FIG. 10a is a schematic diagram of an optical limiter in accordance with the invention.

FIG. 10a illustrates one form of a passive optical apparatus 10. The apparatus 10 includes a shield 12 of an absorber medium 14 mounted in a frame 16. The absorber medium includes a reverse saturable absorber medium of the invention, specifically, any of the class of compounds known as buckminsterfullerene. The protective apparatus 10 is positioned to protect a sensor 18 comprising a light sensitive material, such as an optoelectronic device or the human eye.

The protective apparatus 10 is placed in a line of sight between the sensor 18 and a light source 20 at which the sensor is directed. Examples of light sources 20 include a laser beam and an arc welder.

In normal operation, the sensor 18 monitors the intensity of light produced by the light source 20. There is the possibility that, on an occasional basis, the intensity of light from the light source 20 increases greatly, such that in the absence of protection, the intensity of light would be so great that the sensor 18 would be damaged. The age by limiting the intensity of light that reaches the sensor 18.

The apparatus depicted in FIG. 10a is illustrative of only one of the many uses to which the protective apparatus 10 of the invention is suitably employed. Many other configurations employing the optical limiting composition of the invention may also be envisioned, and the claims herein are accordingly not limited to the particular configuration used.

The use of the buckminsterfullerenes in optical limiter devices (such as depicted in FIG. 10a) may be in film form or in solution.

In film form, the buckminsterfullerene may be sublimed onto a substantially transparent substrate (not shown). If sublimed, the thickness of the film is on the order of a few thousand Ångstroms to provide about 70% transmission. The actual thickness chosen for a particular application depends on the percent transmission desired and the density of the buckminsterfullerene active species. Film thicknesses may accordingly range from 100 to 100,000 Å.

Due to the fact that the buckminsterfullerene compound does not bond well to itself, it may be preferred to encapsulate the film, such as by use of a capping layer formed thereover. Alternatively, the buckminsterfullerene compound may be embedded in a host matrix of a substantially transparent material. Examples of such host materials include silicon oxide, silicon nitride, silicon oxynitride, and transparent plastics, such as polycarbonate, polymethyl methacrylate, paralene, styrene, and the like. The thickness of such a composite film is on the order a few micrometers to provide about 70% transmission. However, as above, the thickness of such a composite film depends on the percent transmission desired and the concentration of the buckminsterfullerene compound in the host matrix, and accordingly, may range from about 5,000 Å to 100 mm.

Alternatively, the buckminsterfullerene may be dissolved in a solvent, and the resulting solution employed as an optical limiter, such as by sealing between two transparent plates. Examples of suitable solvents include aromatic hydrocarbons, such as benzene and toluene, chlorinated hydrocarbons, such as methylene chloride and chloroform, and polar ethers, such as tetra-hydrofuran. The thickness of the device again depends on the transmission desired and the concentration of the active species in solution.

Figure 10B:
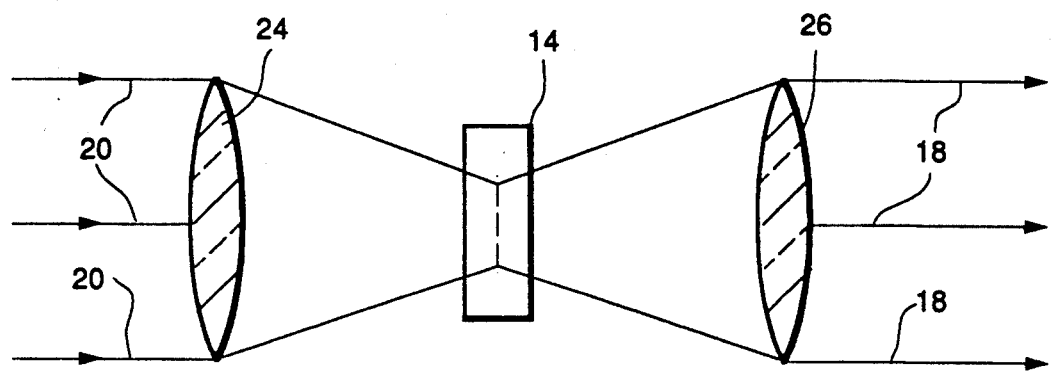
FIG. 10b is a schematic diagram of a focusing geometry utilizing the optical limiter of the invention.

A second embodiment, directed to use of the optical limiter of the invention in a focusing geometry 22, is depicted in FIG. 10b. There, a pair of lenses, 24 and 26, are shown, with an intermediate focal plane 28 located therebetween. The intermediate focal plane permits achieving lower thresholds. The reverse saturable material 14 is located near the focal region 28. Placement at that location provides a threshold that is much lower (as measured at the entrance 24a of lens 24) than without the lenses 24, 26 in place. The buckminsterfullerene material will require lower gains to achieve the same limiting action as other RSA materials.

Specifically, focusing lens 24 converges the input lens area to the area of the focal region 28. The fluence or concentration of light at the focal region is therefore increased by the change in the ratio of the input lens area to the focal region area. This is defined as the gain. The optical limiting material 14 is placed at the focal region 28 to take advantage of the higher fluences and thereby activate the material.

For example, if the fluence at the input lens is 40 mJ/cm$^2$ and the gain is 10, then the fluence at the focal region will be 400 mJ/cm$^2$. If a lens is used symmetrically at the exit, the output fluence will be regenerated at 40 mJ/cm$^2$. If a 70% transmitting $C_{60}$ sample is placed in a beam with a fluence of 40 mJ/cm$^2$ (no lenses), the output fluence will be 28 mJ/cm$^2$ because the fluence is not large enough to activate the optical limiting material. If, however, the optical limiting material is place in the focal region of the two lenses previously discussed with a gain of 10, the 400 mJ/cm$^2$ at the focal region will be limited, after propagating through the material, to about 70 mJ/cm$^2$ ($C_{60}$ in toluene, as shown in FIG. 7); which upon expansion and exiting the output lens 26 has a fluence of 7 mJ/cm$^2$.

For a given protection level of optical fluence, the extremely low limiting threshold of $C_{60}$ does not require as high a gain as other limiters used in the lens system. A lower gain is often desirable for dissipation of the energy of the absorbed light over a greater volume, more flexibility in the system design, and a greater safety margin for optical protection. In equipment such as telescopes, range finders, cameras, and periscopes, an intermediate focal region already exists, and modification is accordingly minor.

Thus, there has been disclosed the use of buckminsterfullerenes in optical limiter applications. It will be apparent to those skilled in this art that various changes and modifications of an obvious nature may be made without departing from the spirit of the invention, and all such changes and modifications are considered to fall within the scope of the invention, as defined by the appended claims.

What is claimed is:

1. A method for protecting an optically sensitive material from light from a light source of high intensity while permitting it to receive light of low intensity, comprising the step of placing between said light source and said optically sensitive material a semi-transparent absorber medium including a reverse saturable absorber consisting essentially of at least one buckminsterfullerene or a derivative thereof having the buckminsterfullerene structure.

2. The method of claim 1 wherein said buckminsterfullerene is selected from the group consisting of $C_{60}$, $C_{70}$, $C_{76}$, $C_{84}$, $C_{90}$, and $C_{94}$.

3. The method of claim 1 wherein said derivative of buckminsterfullerene is selected from the group consisting of $C_{59}B$, $C_{60}$ clathrating an atom, buckminsterfullerene having at least one nucleophilic ligand associated with at least one carbon atom thereof, buckminsterfullerene having at least one organometallic complex associated with at least one carbon atom thereof, and $C_{70}O$.

4. The method of claim 3 wherein said ligand is selected from the group consisting of methyl and ethylenediamine.

5. The method of claim 3 wherein said organometallic compound comprises a multiply-bonded transition metal having a plurality of ligands associated therewith, with said transition metal selected from the group consisting of osmium, ruthenium, and platinum, and with said ligand selected from the group consisting of pyridine, tert-butyl pyridine, acetonitrile, and triphenylphosphine.

6. The method of claim 1 wherein said reverse saturable absorber formed as a film.

7. The method of claim 6 wherein said reverse saturable absorber is sublimed onto a substantially transparent substrate.

8. The method of claim 7 wherein said film of said reverse saturable absorber is a few thousand Ångstroms in thickness for 70% transmission.

9. The method of claim 1 wherein said reverse saturable absorber is embedded in a transparent host material selected from the group consisting of silicon oxide, silicon nitride, silicon oxynitride, and transparent plastics to form a composite film.

10. The method of claim 9 wherein said composite film is about a few micrometers in thickness for 70% transmission.

11. The method of claim 1 wherein said reverse saturable absorber is dissolved in solution.

12. The method of claim 11 wherein said reverse saturable absorber is dissolved in a solvent selected from the group consisting of aromatic hydrocarbons, chlorinated hydrocarbons, and polar ethers.

13. The method of claim 12 wherein said aromatic hydrocarbon is selected from the group consisting of benzene and toluene, said chlorinated hydrocarbon is selected from the group consisting of methylene chloride and chloroform, and said polar ether is tetrahydrofuran.

14. A method for protecting an optically sensitive material from light from a light source of high intensity while permitting it to receive light of low intensity, comprising the step of placing between said light source and said optically sensitive material a semi-transparent absorber medium including a reverse saturable absorber consisting essentially of $C_{60}$.

15. The method of claim 14 wherein said $C_{60}$ is formed as a film.

16. The method of claim 15 wherein said $C_{60}$ is sublimed onto a substantially transparent substrate.

17. The method of claim 16 wherein said film of said $C_{60}$ is a few thousand Ångstroms in thickness to provide 70% transmission.

18. The method of claim 14 wherein said $C_{60}$ is embedded in a transparent host material selected from the group consisting of silicon oxide, silicon nitride, silicon oxynitride, and transparent plastics to form a composite film.

19. The method of claim 18 wherein said composite film is about a few micrometers in thickness to provide 70% transmission.

20. The method of claim 14 wherein said $C_{60}$ is dissolved in solution.

21. The method of claim 20 wherein said $C_{60}$ is dissolved in a solvent selected from the group consisting of aromatic hydrocarbons, chlorinated hydrocarbons, and polar ethers.

22. The method of claim 21 wherein said aromatic hydrocarbon is selected from the group consisting of benzene and toluene, said chlorinated hydrocarbon is selected from the group consisting of methylene chloride and chloroform, and said polar ether is tetrahydrofuran.

23. A passive optical protector, comprising a shield formed of a semi-transparent absorber medium including a reverse saturable absorber consisting essentially of at least one buckminsterfullerene or a derivative thereof having the buckminsterfullerene structure.

24. A passive optical protector, comprising a shield formed of a semi-transparent absorber medium including a reverse saturable absorber consisting essentially of $C_{60}$.

25. A focusing lens array including a pair of lenses forming an intermediate focal plane therebetween and a layer of reverse saturable absorber located at or near said focal plane, said reverse saturable absorber consisting essentially of at least one buckminsterfullerene or a derivative thereof having the buckminsterfullerene structure.

26. A focusing lens array including a pair of lenses forming an intermediate focal plane therebetween and a layer of reverse saturable absorber located at or near said focal plane, said reverse saturable absorber consisting essentially of $C_{60}$.

* * * * *